US006342225B1

(12) United States Patent
Jones et al.

(10) Patent No.: US 6,342,225 B1
(45) Date of Patent: *Jan. 29, 2002

(54) PHARMACEUTICAL ACTIVE CONJUGATES

(75) Inventors: Henry R. Jones; Fariba Shojaee-Moradi; Peter Henri Sonksen, all of London (GB); Dietrich Brandenburg, Reichelsheim (DE); Achim Schuttler, Aachen (DE); Heike Eckey, Höxter (DE); Erik Sundermann, Leverkusen (DE)

(73) Assignees: Deutshces Wollforschungsinstitut, Aachen (DE); Kings College London, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/618,215

(22) Filed: Jul. 18, 2000

Related U.S. Application Data (60) Continuation-in-part of application No. 09/547,870, filed on Apr. 12, 2000, now abandoned, which is a continuation of application No. 09/097,535, filed on Jun. 15, 1998, now Pat. No. 6,063,761, which is a division of application No. 08/596,285, filed as application No. PCT/GB94/01784 on Aug. 15, 1994, now Pat. No. 5,854,208.

(30) Foreign Application Priority Data

Aug. 13, 1993 (GB) .............................. 9316895

(51) Int. Cl.$^7$ ...................... A61K 39/385; A61K 38/28; C07K 16/00
(52) U.S. Cl. ......................... 424/193.1; 514/3; 530/303; 530/389.2; 530/391.7
(58) Field of Search .............................. 530/303, 389.2, 530/391.7; 424/193.1; 514/3

(56) References Cited

U.S. PATENT DOCUMENTS

| 5,268,453 A |   | 12/1993 | Andy et al. .................. 530/303 |
| 5,854,208 A | * | 12/1998 | Jones et al. ..................... 514/3 |
| 6,063,761 A | * | 5/2000  | Jones et al. ..................... 514/3 |

FOREIGN PATENT DOCUMENTS

| EP | 0242416 | 10/1987 |
| WO | 9012814 | 11/1990 |
| WO | 9112817 | 9/1991 |
| WO | 9200322 | 1/1992 |
| WO | 9215611 | 9/1992 |
| WO | 9507931 | 3/1995 |

OTHER PUBLICATIONS

Windhoz et al. The Merck Index, 10$^{th}$, p. 723 abstract No. 4866 (1983).
Chemical Abstracts (99:116795m) Kaliman et al. (1983).

J. Brange et al., Diabetes Care, vol. 13, No. 9 "Monomeric Insulins and Their Experimental and Clinical Implications" 9, Sep. 1990, pp. 923–925.

Ronald S. Spangler, "Selective insulinization of liver in conscious diabetic dogs", Am. J. Physiol. 249 (Endocrinal. Metab. 12) pp. E152–159 (1985).

J. Markussen et al., Soluble, fatty acid acylated insulins bind to albumin and show protracted action in pigs, No. 262, pp. 002–009.

Journal of Controlled Release, (1992), pp. 179–188, Trials of Lipid modification of piptide hormones for intestinal delivery.

Pharmaceutical Research, vol. 6, No. 2, (1989), Synthesis of Palmitoyl Derivatives of Insulin and Their Biological Activities.

Proceedings of the Second International Insulin Symposium Aachen, Germany, Sep. 4–7, 1979, Insulin Chemistry, Structure and Function of Insulin and Related Hormones.

F. Shojaee–Moradi, et al., "Convalent Insulin Dimers Are Hepatoselective", Abstract, Medical and Scientific Section, Apr. 13–15, 1989.

Snyder, S. M. et al. "The Binding of Thyroid Hormone Analogues to Thyrozine–Binding Globulin (TBG)", in Thyroid Research (Robbin J. and Braverman L. E. eds.) (1976) pp. 297 to 299.

Snyder, S.M. et al. (1976) Binding of Thyroid Hormones and their Analogues to Thyroxin–Binding Globulin in Human Serum, J. Biol. Chem. 251 (21), 6489 to 6494.

Robbins, J. et al. "Plasma Transport of Thyroid Hormones" from Thyroid Hormone Metabolism (Hennemann, G. ed.) 1986, 3 to 38.

* cited by examiner

Primary Examiner—Kevin E. Weddington
(74) Attorney, Agent, or Firm—Sughrue Mion, PLLC (57) ABSTRACT

The invention provides an analogue of a pharmaceutical active whose molecular weight is less than 25,000 Daltons, the analogue comprising a pharmaceutical active whose molecular weight is less than 25,000 Daltons covalently linked to a pendant molecular group wherein as a result of the administration of the composition to the human or animal body an active complex having a molecular weight of 25,000 Daltons or greater is present in the human or animal circulatory system. The analogue is hepatoselective when administered to the circulatory system. Preferably the analogue is an insulin analogue comprising an insulin or functional equivalent thereof covalently linked to the pendant molecular group wherein the active complex is an insulin complex. Such an insulin analogue may be used in a method of insulin replacement therapy.

18 Claims, 8 Drawing Sheets

PHARMACEUTICAL ACTIVE CONJUGATES

This application is a continuation-in-part of Ser. No. 09/547,870, filed Apr. 12, 2000, now abandoned which was a continuation of Ser. No. 09/097,535 filed Jun. 15, 1998 (now U.S. Pat. No. 6,063,761 dated May 16, 2000), which is a divisional of Ser. No. 08/596,285 filed Feb. 13, 1996, now U.S. Pat. No. 5,854,208 dated Dec. 29, 1998 which was a section 371 application of PCT/GB94/01784 filed Aug. 15, 1994.

The present invention relates to novel hepatoselective pharmaceutical actives. In particular it relates to novel hepatoselective insulin analogues suitable for use in an improved treatment of diabetes mellitus.

When drugs and other pharmaceutical actives are administered to the human or animal body it may be required that the active is needed to be present primarily in the liver or to act primarily on the tissues of the liver. That is, the active is required to be hepatoselective. Achieving hepatoselectivity can be difficult, in particular where the active is administered by injection into the skin. One case in which achievement of hepatoselectivity would be especially desirable is the administration of insulin.

The hormone insulin, secreted by the pancreas, has various important roles to play in glucose metabolism. In the liver, after binding to cell surface receptors, insulin promotes the conversion of glucose to glycogen (glycogenesis), promotes protein synthesis and inhibits fat breakdown. Insulin deficiency results in breakdown of glycogen (glycogenolysis), protein and conversion of products of fat and protein breakdown to glucose (gluconeogenesis) leading to a raised plasma glucose level (hyperglycaemia). In subjects who produce adequate amounts of insulin the blood glucose level remains within a certain range. Any excess of glucose is stored in the liver and muscles as glycogen.

Insulin also acts on cell membrane receptors in other tissues to enhance the entry of glucose into cells, thereby diminishing the plasma glucose concentration.

Thus insulin acts to reduce the plasma glucose level by reducing the production of glucose by the liver and by increasing uptake and metabolism of glucose by the liver and by increasing uptake and metabolism of glucose by peripheral tissues.

Deficiency of insulin due to disease of the islets of Langerhans and/or deficiency of insulin action results in diabetes mellitus, a condition in which the blood glucose concentration is high.

In subjects who are not diabetic insulin is produced in the pancreas and transported directly to the hepatic circulation and hence is transported to the liver before any other organs or regions of the body. Thus the liver experiences a very high exposure to the insulin produced. Usually at least 50% of the insulin produced is bound to receptors in the liver, and hence acts in the liver. Insulin bound to receptors in the liver is removed from the circulation and degraded by the liver cells. The insulin which is not bound in the liver and hence passes to the peripheral circulation is therefore at a much lower concentration. Thus the peripheral tissues (eg fat and muscle) which are also targets of the insulin experience a smaller exposure to the insulin secreted.

In diabetic subjects treatment is often carried out by insulin-replacement therapy. In general an insulin preparation is injected subcutaneously. The most common subcutaneous insulin regimen involves twice-daily injection of mixtures of short- and intermediate-acting insulin preparations. Insulin is absorbed from the subcutis into the peripheral circulation and thence to the entire body, including the liver. With such a system the liver and the peripheral tissues tend to experience approximately equal exposure to insulin.

There are various disadvantages and negative side-effects with the use of this system.

First, if sufficient insulin is injected to enable a high enough concentration to be present in the hepatic circulation then too high a concentration will be present in the peripheral circulation. Similarly if a suitable concentration is present in the peripheral circulation the concentration of insulin in the hepatic circulation will be inadequate.

There is believed to be a danger associated with high concentrations of insulin in the peripheral circulation (hyperinsulinaemia) of cardiovascular disease.

Second, there is a serious risk of hypoglycaemia in diabetic subjects receiving insulin replacement therapy by subcutaneous injection. A concentration of insulin in the peripheral circulation which is too high can lead to a blood sugar level which is too low and subsequent collapse.

It would therefore be desirable to be able to direct a large concentration of insulin directly to the hepatic insulin receptors with a lower concentration of insulin being directed to the peripheral insulin receptors. It would also be desirable to achieve such hepatoselectivity for other active molecules.

Some attempts have been made to obtain the desired hepatoselectivity of insulin. Intravenous injection directly into the hepatic portal circulation could allow injected insulin to pass directly to the liver before reaching the peripheral circulation. Such a system is unsuitable for general use due to the difficulty and complicated nature of its operation; in particular it is not suitable for use by diabetic patients themselves except under exceptional circumstances.

An attempt has been made to render insulin hepatoselective by injecting it subcutaneously whilst encapsulated in lipid vesicles. (Spangler, Ronald S., "Selective Insulinisation of Liver in Conscious Diabetic Dogs", Am. J. Physiol. 249 (Endocrinol. Metab. 12): E152–E159, 1985). Insulin encapsulated in lipid vesicles (designated vesicle encapsulated insulin VEI) was targeted to hepatocytes by means of a digalactosyl diglyceride moiety incorporated on the outside of the lipid vesicles. Using this approach it was possible to alter the distribution of an administered glucose load to favour hepatic deposition.

The present inventors have found (British Diabetic Association Medical and Scientific section Conference, Manchester, April 13–15, 1989) that covalent dimers of insulin (molecular weight ±12,000 Daltons rather than ±6,000 for insulin monomer) have a greater effect on hepatic glucose output than on peripheral uptake and utilisation. That is, the covalent insulin dimers appear to act preferentially on hepatocytes rather than on cells of the peripheral tissues. It has also been found that proinsulin shows this hepatoslectivity to a smaller degree. Proinsulin is the zymogen which is cleaved to form the active hormone insulin. The proinsulin molecule is larger than the active insulin molecule.

The cells of the peripheral tissues, for instance fat and muscle, are separated from the blood vessels by the capillary endothelium. In the liver however there is no such barrier between blood vessels and hepatocytes.

It is thought that transport across the capillary endothelium is mainly by diffusion i.e. active transport of insulin across the capillary endothelium does not occur to any significant extent. Therefore the present inventors believe that the absorption of insulin into the peripheral tissues is determined by factors influencing diffusive transport, in particular by steric hindrance or size of molecules. This is believed to be a reason for the relative hepatoselectivity of covalent insulin dimers and proinsulin when compared with insulin monomers; both have free access to hepatocytes but the larger covalent insulin dimer or proinsulin is absorbed into the peripheral tissues from the bloodstream more slowly than is the insulin monomer. Thus the larger molecules spend a longer time in the bloodstream before being absorbed into the peripheral tissues and are thus are more likely to reach the liver, where they may be active more easily.

According to the present invention there is provided the use of an analogue of a pharmaceutical active whose molecular weight is less than 25,000 Daltons in the manufacture of a composition for use in a method of treatment of the human or animal body, the analogue comprising a pharmaceutical active whose molecular weight is less than 25,000 Daltons covalently linked to a pendant molecular group wherein as a result of the administration of the composition to the human or animal body an active complex having a molecular weight of 25,000 Daltons or greater is present in the human or animal circulatory system.

The invention is of particular usefulness when the analogue is an insulin analogue which comprises an insulin or functional equivalent thereof covalently linked to a pendant molecular group, so that as a result of the administration of the composition to the human or animal body an insulin complex having a molecular weight of 25,000 Daltons or greater is present in the human or animal circulatory system. This invention is also applicable to other pharmaceutical actives of molecular weight below 25,000 Daltons which are administered so as to enter the circulatory system and which are required to be hepatoselective and for which similar problems as those encountered with the administration of insulin therefore also apply. In this specification the invention is discussed primarily in terms of its use for giving hepatoselectivity to insulin or a functional equivalent thereof, but it will be understood that the disclosures made are equally applicable to other pharmaceutical actives of molecular weight less than 25,000 Daltons.

According to a first, particularly preferred, embodiment of the invention the pendant molecular group has an affinity for one or more binding proteins present in the human or animal circulatory system wherein the total molecular weight of the insulin or functional equivalent thereof (or other pharmaceutical active) and the additional molecular group and the one or more binding proteins is 25,000 Daltons or greater.

Binding proteins "in the human or animal circulatory system" are those which are present in the blood plasma.

Thus when the analogue is introduced into the bloodstream the one or more binding proteins will become non-covalently linked to the additional molecular group, forming a complex which has a molecular weight of 25,000 Daltons or greater.

According to a second embodiment of the invention an insulin analogue (or analogue of another pharmaceutical active) is used which additionally comprises one or more binding proteins non-covalently attached to the pendant molecular group wherein the total molecular weight of the insulin or functional equivalent thereof (or other pharmaceutical active) and the pendant molecular group and the one or more binding proteins is 25,000 or greater.

In this second embodiment the analogue is a complex having a molecular weight of 25,000 or greater and may be administered into the circulatory system as such, for instance intravenously.

According to a third embodiment of the invention an insulin analogue (or analogue of other pharmaceutical active) is used in which the total molecular weight of the insulin or functional equivalent thereof (or other pharmaceutical active) and the covalently linked pendant molecular group is 25,000 Daltons or greater.

As with the second embodiment, the analogue is a complex having a molecular weight of 25,000 or greater and may be administered into the circulatory system as such, for instance intravenously.

For use in the first aspect of the present invention there is provided an analogue of a pharmaceutical active whose molecular weight is less than 25,000 Daltons comprising a pharmaceutical active whose molecular weight is less than 25,000 Daltons covalently linked to a pendant molecular group, said pendant molecular group having an affinity for one or more binding proteins present in the human or animal circulatory system.

As explained above, the invention is especially useful when the compound is an insulin analogue comprising an insulin or functional equivalent thereof covalently linked to a pendant molecular group which has an affinity for one or more binding proteins present in the human or animal circulatory system.

Such an insulin analogue (or analogue of other pharmaceutical active) may be injected subcutaneously and absorbed into the bloodstream through the capillary endothelium without difficulty. When in the bloodstream the insulin analogue will come into contact with the binding protein for which the covalently-linked pendant molecular group has an affinity. Thus at least some molecules of the insulin analogue will become bound to the said binding protein, forming an insulin complex. Binding proteins tend to be bulky molecules of high molecular weight. They therefore tend not to diffuse out through the capillary endothelium easily and remain in the bloodstream. Thus the effective size of molecule and hence the molecular weight of the bound insulin analogue is increased dramatically. Absorption from the blood vessels into the peripheral tissues, for instance fat and muscle, through the capillary endothelium is now greatly inhibited due to the attachment of the insulin analogue to the high molecular weight binding protein. In the liver however there is no such barrier therefore the insulin analogue even with the associated binding protein may have access to the hepatocyte insulin receptors essentially to the same degree as would conventional insulin.

In the same way an analogue of another pharmaceutical active may be induced not to diffuse out through the capillary endothelium and to remain in the bloodstream until it is carried to the liver where it may act or be taken up as required.

Binding of the pendant molecular group and the binding protein is not covalent. Binding forces may be for instance electrostatic (eg attraction of opposite charges, hydrogen bonding) or hydrophobic. Thus binding is not permanent. The insulin analogue (or analogue of other pharmaceutical active) may be absorbed onto the hepatic tissues in its bound form. Molecules of the insulin analogue which have not been bound by the binding protein or which have become bound and subsequently unbound are capable of passing through the capillary endothelium into the peripheral tissues.

The covalently-linked molecular group is attached in such a way that the active site (or sites) of the insulin equivalent or other pharmaceutical active remains available to carry out its prescribed functions.

Attachment of a suitable molecular group to the insulin equivalent (or other active) may be carried out by conventional chemical methods known to those skilled in the art.

According to this aspect of the invention there is also provided a method of insulin replacement therapy comprising subcutaneous injection of a preparation comprising an insulin analogue as described above.

Preferred features of the first embodiment of the invention will now be described in detail.

The insulin or functional equivalent thereof, when insulin is the active used, may be any of the insulins conventionally used in insulin replacement therapy.

J. Brange et al ("Monomeric Insulins and their Experimental and Clinical Implications", Diabetes Care, vol. 13, no. 9, September 1990) and others have studied the possibility of developing insulins with reduced tendencies to self-association. These insulins are absorbed from the subcutis into the bloodstream more rapidly than is the form in which insulin is usually found in pharmaceutical formulations. Insulin assumes an associated state in pharmaceutical formulation. Six monomers of insulin associate to form hexamers. The association is non-covalent. With the use of DNA technology Brange et al and others have prepared insulins which remain dimeric or even monomeric at high (pharmaceutical) concentration by the introduction of one or a few amino acid substitutions into human insulin. Insulins with reduced association capacity as described by Brange et al and others are preferred for use as the insulin equivalent to which the additional molecular group is attached. When the pharmaceutical active is an insulin equivalent such insulins are preferred, because their reduced tendency to self-associate means that they are more rapidly absorbed into the bloodstream from the subcutis than are conventional insulins which tend to be injected in hexameric form.

Insulins of this type have also been developed by Eli Lilly. These are described in Protein Engineering, Vol 5, 519–525 and 527–533 (1992) (both D. N. Brems et al) Studies of amino acid modified monomeric insulins have also been described in Diabetes 40 Suppl. 1 (1991), 423A (Howey et al) and 464A (Shaw et al).

The pendant molecular group covalently linked to the insulin equivalent or other active may be any molecular group which has an affinity for a binding protein present in the circulatory system and which will not itself act in the body to give detrimental effects. The molecular group chosen should usually be of a molecular weight similar to or less than that of the insulin equivalent or other active. Preferably the total molecular weight of the insulin or functional equivalent thereof or other active and the additional molecular group is less than 25,000, more preferably less than 20,000 or 15,000, and may be less than 12,000. This is in order that attachment of the pendant molecular group to the insulin equivalent or other active to form the analogue should not hinder the passage by diffusion of the injected analogue from the subcutis through the capillary endothelium into the bloodstream. Preferred molecular groups are molecular structures which possess an affinity for one or more proteins which are naturally present in the circulation. They may be based on naturally-occurring hormones or on functional equivalents of such hormones which also possess affinity to their binding proteins or they may be based on other substances for which such binding proteins exist. The pendant molecular group should be harmless when injected into the body; this may be achieved for instance by ensuring that the concentration of insulin analogue or analogue of other active in the bloodstream is high enough to allow the beneficial effects of insulin or other therapy to be felt but low enough to prevent any effects which might be due to the pendant molecular group being felt, or by ensuring that the insulin analogue or analogue of other active is not present in parts of the body where the pendant molecular group might be active, or by rendering the pendant molecular group inactive by structural modification which nevertheless preserves its ability to bind to its binding protein.

The pendant molecular group may be itself an insulin equivalent, for instance insulin-like growth factor 1 (IGF1). This polypeptide has an affinity for IGF1 binding proteins, which circulate naturally in the human bloodstream.

The pendant molecular group may be a native or modified thyroxyl group, derived from the human thyroid hormone thyroxine 3,5,3',51'-L-tetraiodothyronine (T4). There are several binding proteins present in the human circulatory system which have an affinity for the T4 group, for instance thyroxine binding globulin (TBG), thyroxine binding prealbumin (TBPA) and albumin. These proteins are known collectively as thyroxine binding proteins (TBP).

Other suitable groups derived from hormones or their functional equivalents may be used. Suitable groups may be ascertained by a skilled person using methods known in the pharmaceutical field.

The pendant molecular group with an affinity for a binding protein may be covalently attached directly to the insulin equivalent (or other active), as explained above in a place chosen so that the additional molecular group does not inhibit the action of the insulin equivalent. The structure of insulin and the locations of its active sites are well known, therefore when insulin is used those skilled in the art will be able to establish appropriate positions at which to attach the said molecular group so as not to interfere significantly with the action of the insulin or equivalent.

Alternatively a short molecular chain (or "spacer arm") may be used to link the insulin equivalent (or other active) and the said molecular group. The spacer arm is linked covalently both to the insulin equivalent and to the pendant molecular group. Such a spacer arm ensures that the insulin equivalent and binding protein are distanced from one another, thus preventing substantial interference with insulin activity by the (usually bulky) high molecular weight binding protein. The spacer arm is usually a linear chain, preferably of from 3–10 carbon atoms in length. Such a spacer arm may be for instance an aminohexanoyl (AH) group, which is a six-carbon chain. Other groups may of course be used as a spacer arm. For example aminoacids either singly or linked as small peptide sequences could be used.

It should be ensured that the binding protein which has an affinity for the pendant molecular group is present in the blood plasma in sufficiently large amounts that the trapping of the binding protein by the insulin analogue (or analogue of other active) with the covalently linked molecular group will not deplete the levels of binding protein in the blood to detrimental effect. For instance the level of binding protein should not be depleted so that insufficient binding protein is available to carry out its usual function in the body, if any.

The insulin analogue (or analogue of other active) of the invention may be produced by various methods, for instance: chemical reaction of the insulin or insulin equivalent or other active with a substance or substances which include the pendant molecular group; protein synthesis of the complete analogue; production by a genetically engineered micro organism.

The insulin analogue of the invention may be used in a method of insulin replacement therapy.

An insulin analogue according to the invention or a mixture of two or more different insulin analogues according to the invention form part of an insulin preparation. This insulin preparation is suitable for use in a method of treatment of the human or animal body, preferably suitable for subcutaneous injection, and may comprise a treatment for diabetes. Additional ingredients may be added which modify the rate of absorption from the subcutaneous depot into the circulation. The insulin-based preparation preferably is suitable for subcutaneous injection, in which case it is therefore suitable for use by sufferers from diabetes on themselves.

The insulin preparation may comprise the hepatoselective insulin analogue of the invention and a conventional non-hepatoselective insulin. On subcutaneous injection and passing into the bloodstream the conventional insulin will act in the peripheral tissues whilst the insulin analogue of the invention provides a controlled, hepatoselective action.

The analogues of other pharmaceuticals actives of the invention may also be used in methods of treatment of therapy by subcutaneous injection of a preparation comprising the analogue of the actives.

According to the second embodiment of the invention an insulin analogue (or analogues of other active) with a covalently attached pendant molecular group is used with a binding protein already non-covalently linked to the pendant molecular group. A composition comprising such an insulin analogue would be more suitable for intravenous administration than for subcutaneous administration due to the very high molecular weight of the insulin analogue in the composition (as compared with the insulin analogue of the first embodiment, which forms an insulin complex of molecular weight greater than 25,000 only after administration into the circulatory system). It may be desirable in some cases however to provide such an insulin analogue or analogues of other active for use in the manufacture of a composition suitable for intravenous administration.

The pendant molecular group and binding proteins may be any of those described above as suitable for the first embodiment of the invention. In addition the binding proteins may be proteins which do not occur naturally in the human or animal circulatory system (and which are harmless when introduced into the circulatory system) and the pendant molecular group may be any group with an affinity to such a protein.

According to a third embodiment of the invention an insulin analogue (or analogue of other active) is used which comprises an insulin or functional equivalent thereof (or other active) with a large group covalently attached. Such a group should be large enough that the entire insulin analogue has a molecular weight of at least 25,000. It should also, like the pendant molecular group of the first embodiment of the invention, be harmless when introduced into the body. This may be achieved as described above for the pendant molecular group. The large molecular group of the third embodiment of the invention may for instance be based on a polypeptide structure or on other suitable polymeric structures.

The analogues of the second and third embodiments of the invention may be produced by the methods mentioned above as suitable for the production of the analogue of the first embodiment of the invention. For instance suitable methods in the case of the analogue of the third embodiment include chemical reaction of the insulin or equivalent or other active with a substance or substances which include the covalently linked molecular group, protein synthesis of the complete analogue and production by a genetically engineered micro organism. In the case of the second embodiment the section of the analogue comprising the insulin or equivalent or other active and the additional molecular group may be synthesized in the same way as may be the analogue of the first embodiment. The binding protein may be synthesized for instance by protein synthesis, production by a genetically engineered micro organism, extraction from a naturally-occurring organism. Non-covalent attachment of the binding protein or proteins to the pendant molecular group may be achieved by methods known in the art.

The analogues of the second and third aspects of the invention are suitable for incorporation in compositions which are to be administered intravenously. Where the active is insulin or a functional equivalent thereof, such compositions may be used in a method of insulin replacement therapy. Such compositions comprise one or more insulin analogues of the second and third embodiments of the invention. The composition may also comprise additional ingredients which may be chosen by those skilled in the art.

EXAMPLES

The present inventors have undertaken a study to explore the possibility that insulin analogues with restricted access to peripheral tissues may display relative hepatoselectivity in vivo.

Analogues of insulin which include a thyroxyl moiety which binds to thyroid hormone binding protein (TBP) have been designed and tested. $N^{\alpha B1}$-thyroxyl-insulin (T4-Ins) and $N^{\alpha B1}$-thyroxyl-aminohexanoyl insulin (T4-AH-Ins) were synthesized using methods of chemical synthesis given below.

Preparation of Thyroxyl Insulins
Abbreviations

Msc = methylsulphonylethyloxycarbonyl

Boc = tert. butyloxycarbonyl

DMF = dimethylformamide

DMSO = dimethylsulfoxide mp = melting point

ONSU = N-oxysuccinimide ester

Example 1
B1-thyroxyl-insulin (Porcine) (T4-Ins)
Protected Thyroxine Derivatives
Msc-L-thyroxine (I)

776 mg (1 mmol) L-thyroxine in 2 ml dimethylsulfoxide was reacted with 530 mg (2 mmol) Msc-ONSu in the presence of 139 µl (1 mmol) triethylamine at room temperature for 18 hours. After concentration in vacuo the oily residue was taken up in ethyl acetate, the organic layer washed with water, dried over $Na_2SO_4$, and the solvent removed in vacuo. The solid residue was crystallised from hexane.

Yield: 651 mg (70.2% of theory),
mp: 200° C.
Msc-L-thyroxine-N-oxysuccinimide Ester (II)

To a cooled (0° C.) solution of 371 mg (0.4 mmol) of Msc-thyroxine and 40 mg (0.4 mmol) N-hydroxysuccinimide in 1 ml tetrahydrofurane a precooled solution of 82.5 mg N,N'-dicyclohexycarbodiimide in 0.5 ml tetrahydrofurane was added under stirring. After further stirring for 3 hours the precipitate was removed by filtration, and the filtrate concentrated in vacuo. Crystallisation of the solid residue from methylenechloride/petroleum ether.

Yield: 295 mg (71%, based on I)
mp: 180° C.

B1-thyroxyl-insulin (Porcine) (III)

To a solution of 100 mg (approx 0.016 mmol) A1,B29-Msc$_2$-insulin (prepared according to Schüttler and Brandenburg, Hoppe-Seyler's Z. Physiol, Chem. 360, 1721–1725 (1979)) and 18 µl (0.160 mmol) N-methylmorpholine in 2 ml of DMSO 116.4 ml (0.160 mmol) of II in 0.2 ml DMSO were added. After stirring for 6 h at room temperature the insulin derivative was precipitated with ether/methanol (9:1, v/v), isolated by centrifugation, washed 3 times with ether/methanol, and dried in vacuo.

Msc groups were removed by treatment with NaOH/dioxane/methanol at 0° C., and III was purified by gel filtration on Sephadex G 50 fine as described (Geiger et al, Chem. Ber. 108, 2758–2763 (1975)). Lyophilization gave 78.4 mg B1-thyroxyl-insulin (75%, based on Msc$_2$-insulin).

Example 2

B1-thyroxyl-aminohexanol-insulin (Porcine) (IV) (T4-AH-Ins)

1. BOC-ε-aminohexanoic acid was prepared by reacting 1.32 g (10 mmol) ε-aminohexanoic acid with 2.4 g (11 mmol) di-tert.butyldicarbonate in dioxane/water at pH 9 and was obtained in 87% yield (2.2 g). Mp after recrystallisation from ethyl acetate: 75° C.
2. 22.8 mg (0.096 mmol) Boc-aminohexanoic acid was preactivated with 13 mg 1-hydroxybenzotriazole and 17.8 mg (0.09 mmol) dicyclohexyl carbodiimide in 0.7 ml dimethylformamide for 1 h at 0° C. and 1 further hour at room temperature.
3. Then, a solution of 100 mg (approx. 0.016 mmol) A1,B29-Msc$_2$-insulin and 18 µl (0.160 mmol) N-methylmorpholine in 1 ml of DMF was added. After stirring for 70 minutes at room temperature the mixtures was filtered, and the insulin derivative was precipitated with ethyl ether/methanol (9:1, v/v), isolated by centrifugation, washed 3 times with ether/methanol, and dried in vacuo.
4. The Boc protecting group was cleaved by treatment of the product with 3 ml trifluoro acetic acid for 1 hour at room temperature. The solution was concentrated in vacuo, the insulin derivative precipitated with ether, isolated, washed with ether, and dried. Yield: 77.8 mg of B1-aminohexyl-A1,B29-Msc$_2$-insulin.
5. 102 mg (0.016 mmol) of this derivative was dissolved in 2 ml dimethylformamide and 18 µl (0.16 mmol) N-methylmorpholine. After addition of 116 mg (0.16 mmol) Msc-thyroxine-N-oxysuccinimide ester in 0.2 ml dimethylformamide the mixture was stirred for 3 hours at room temperature. The protected insulin was isolated by precipitation with methanol/ether and isolated as described above.
6. Msc groups were removed by treatment with NaOH/dioxane/methanol at 0° C., and IV was purified by gel filtration on Sephadex G 50 fine as described (Geiger et al. op. cit.). Lyophilization gave 39.1 mg B1-thyroxyl-aminohexanoyl-insulin (37%, based on aminohexyl-Msc$_2$-insulin).

T4-Ins, T4-AH-Ins and insulin (Ins) were infused into four anaesthetized beagles with D-$^3$H-3-glucose for measurement of the rates of glucose production (Ra) and glucose disposal (Rd). Euglycaemia and glucose specific activity were maintained by variable infusion of D-glucose with D-$^3$H-3-glucose.

With all three materials glucose Rd was increased and glucose Ra decreased from basal level 2.70±0.19 mg. kg$^{-1}$ min$^{-1}$, (p<0.05). In each experiment insulin-like activity for Ra and Rd was calculated as the area between the basal values of each of these variables and subsequent values plotted graphically against time (AUC). For Ins, T4-Ins and T4-AH-Ins respectively, AUC for Ra values were −431±121, −226±154 and −357±50 (mean±SEM, mg/kg), (no significant differences) and AUC for Rd values were 1142±160, 629±125 and 830±178 mg/kg, both analogues different from Ins p<0.05.

These results indicate that insulin analogues of the invention act to a greater extent on the tissues of the liver than on those of the peripheral regions of the body, such as fat and muscle.

Example 3

In vitro Binding Studies 3.1 Isolation of Rat Liver Plasma Membrane (LPM)

Rat liver plasma membrane (LPM) was isolated to be used in equilibrium binding assays as the source of insulin receptors. LPM actually contains not only plasma membrane, but also membrane of the nucleus, mitochondria, Golgi bodies, endoplasmic reticulum and lysosomes. When cell membranes are fragmented, they reseal to form small, closed vesicles—microsomes. Therefore, LPM can be separated into a nuclear and a microsomal component. Each component can be separated into a light and a heavy fraction, which in turn, can be separated into further subfractions. Plasma membranes, where insulin receptors reside, are found in the light fractions, but the present aim was to obtain the microsomal light fraction only, since the nuclear light fraction usually produces variable results in the binding assay. The method first described by Neville (1960) was used to isolate plasma membrane fractions from fresh rat livers.

3.2.1 Fast Protein Liquid Chromatography (FPLC)

To ascertain the binding of the insulin or the analogue to the thyroid hormone binding proteins (THBPs), they were incubated overnight at 4° C. The bound and unbound species were separated by molecular weight with FPLC. As shown in Table 1, the binding of H-Ins, and LT$_4$-Ins to normal human serum, HSA (human serum albumin) and TBG (thyroxine binding globulin) were studied. The THBP concentrations used were physiological, except TBG, due to reasons of costs.

TABLE 1

The binding of each analogue to each THBP were studied

| Insulin or Insulin Analogues | Thyroid hormone binding proteins (THBPs) | Concentration of THBPs used | Physiological THBP concentration |
|---|---|---|---|
| -H-Ins | -TBG | 0.238 µM | 0.27 µM |
|  | -HSA | 5% (w/v), | 4.24% (w/v), |
| -LT$_4$-Ins | Normal human serum (TBG, albumin, prealumbin) | or 757 µM | or 640 µM |

HSA = human serum albumin
TBG = thyroxine binding globulin 3.2.2 Dilution of THBPs and Incubation with Analogues Solutions (0.5 ml) of THBPs were prepared in FPLC buffer as followed and then vortexed;

Normal human serum—used undiluted.

HSA (5% w/v)—diluted 1:4 from HSA (20% w/v).

TBG—10 µl of stock TBG (0.1 mg/0.13 ml) was added to 0.5 ml buffer. The amount of HSA in the FPLC/Barbitone/HSA buffer (0.2%) was too small to significantly alter the binding of TBG to the analogues.

H-Ins (100 µl of 0.276 µM) or analogues was added to the THBP solution. It was vortexed and incubated at 4° C. for ≈16 hours or overnight. Before FPLC, it was vortexed again, and filtered through a syringe filter of pore size 0.2 μm (Acrodisc® LC13 PVDF from Gelman, UK) to remove bacteria and serum precipitates.

3.2.3 Fractions are Collected from the Column

The fraction tubes (LP3 tubes) were coated with 50 μl 3%(w/v) HSA to prevent the analogues from adsorbing to the tubes' inner surfaces. The fraction size was programmed as 0.50 ml. Immunoreactive insulin in each fraction was assayed with radioimmunoassay on the same day.

3.2.4 Radioimmunoassay (RIA) for Insulin

A double-antibody radioimmunoassay (RIA) was performed to determine the concentrations of H-Ins or insulin analogue in each FPLC fraction, using insulin-specific antibodies.

The assay was calibrated using insulin standards. Before the insulin standards and FPLC fractions can be assayed, their HSA concentrations were standardized, by diluting them with Barbitone/HSA(0.2% w/v) buffer and FPLC/Barbitone/HSA buffer. A double dispenser (Dilutrend, Boehringer Corporation London Ltd) was used to add the appropriate volume of buffer and standard or FPLC fractions into the labelled LP3 tubes. The total volume of each tube was 500 μl. In addition, three tubes of NSB (non-specific binding), containing the standardized HSA concentration, were prepared with Barbitone/HSA(0.2% w/v) and FPLC/Barbitone/HSA buffers. Table 2 summarizes the dilution of the standards and FPLC fractions, as well as the preparation of the TC and NSB tubes.

TABLE 2

Contents of the final assay tubes

| | Final Assay Tubes | | | |
|---|---|---|---|---|
| Contents | TC | NSB | Standard | FPLC fractions |
| Std. Solutions | — | — | 50 | — |
| FPLC/BARBITONE/HSA buffer | — | 350 | 350 | — |
| Barbitone/HSA (0.2%) Buffer | — | 150 | 100 | 150 |
| FPLC sample | — | — | — | 350 |
| [$^{125}$I]insulin tracer | 100 | 100 | 100 | 100 |
| Primary Ab | — | 0 | 100 | 100 |
| Secondary Ab | — | 100 | 100 | 100 |
| Total volume | 100 | 800 | 800 | 800 |

All volumes in μl.
*Replace with 100 μl Barbitone/HSA (0.2% w/v) buffer
Std. = standard; Ab = antibody.

All volumes in μl.
*Replace with 100 μl Barbitone/HSA(0.2% w/v) buffer
Std.=standard; Ab=antibody.

3.2.5 Addition of [$^{125}$I] Insulin Tracer

An aliquot of [$^{125}$I] insulin tracer was added to Barbitone/HSA (0.2% w/v) buffer of an adequate volume (100 μl per tube). The radioactivity in 100 μl of the resulting tracer solution was counted in the γ-counter, and the counts per minute (cpm) should lie between 3000–5000 cpm. ANSA (2 mg/ml) was dissolved in the solution, and it functioned to displace the $T_4$ moieties on the analogues from the THBPs, since the THBP could be shielding the insulin moiety that was to be assayed. Finally, 100 μl of this solution was added to every tube.

3.2.6 Addition of Primary Antibody (W12) and Incubation

The primary antibody, W12, is a polyclonal, guinea-pig anti-insulin antibody. It recognises epitopes away from the B1 residue of the insulin molecule, so that the $T_4$ moiety, which is linked to the B1 residue, will not hinder the binding W12. It was diluted to 1:45,000 in Barbitone/HSA(0.2% w/v) buffer, and 100 μl was added to every tube, except the TC and NSB tubes. Finally the tubes were vortexed in a multi-vortexer (Model 2601, Scientific Manufacturing Industries, USA) and incubated at room temperature for about 16 hours.

3.2.7 Addition of Secondary Antibody (Sac-Cel)

The secondary antibody, Sac-Cel (IDS Ltd., AA-SAC3), is a pH7.4, solid-phase suspension that contains antibody-coated cellulose. It was diluted 1:1 (v/v) with Barbitone/HSA(0.2% w/v), and 100 μl was added to all tubes (except TC), vortexed, and incubated at room temperature for 10 min. 1 ml distilled water was added to the tubes prior to centrifugation to dilute the solution, thereby minimising non-specific binding.

3.2.8 Separation of Free and Bound Species

To separate the free and antibody-bound species, the tubes were centrifuged at 2,500 rpm to 20 min in a refrigerated centrifuge (IEC DPR-6000 Centrifuge, Life Sciences International) set at 4° C. The tubes were then loaded into decanting racks. The supernatant, containing the free species, were decanted, by inverting the trays quickly over a collection tub. Care was taken to prevent the pellet from slipping out, and the tubes were wiped dry to remove the traces of supernatant. The combined supernatant was later disposed according to the laboratory's safety guidelines in the sluice. Finally, the samples, together with the TC and NSB tubes, were counted in the γ-counter using a programme for RIA(RiaCalc).

3.3 Equilibrium Binding Assay

This equilibrium binding assay determines the analogues affinity to the insulin receptors on the LPM, both in the presence and absence of the THBPs. In brief, a fixed amount of [$^{125}$I] insulin tracer was incubated with the analogue at different concentrations, together with a fixed volume of LPM, such that the analogue inhibited the tracer from binding to the insulin receptors. The amount of bound tracer was counted in the γ counter after separating the bound and free species by centrifugation. The results were used to calculate the ED50 (half effective dose) and binding potency estimates relative to H-Ins, or, in assays investigating the effects of added THBPs, relative to the analogue in the absence of THBPs.

3.4 Results 3.4.1 Radioimmunoassay (RIA)

Figure 1:
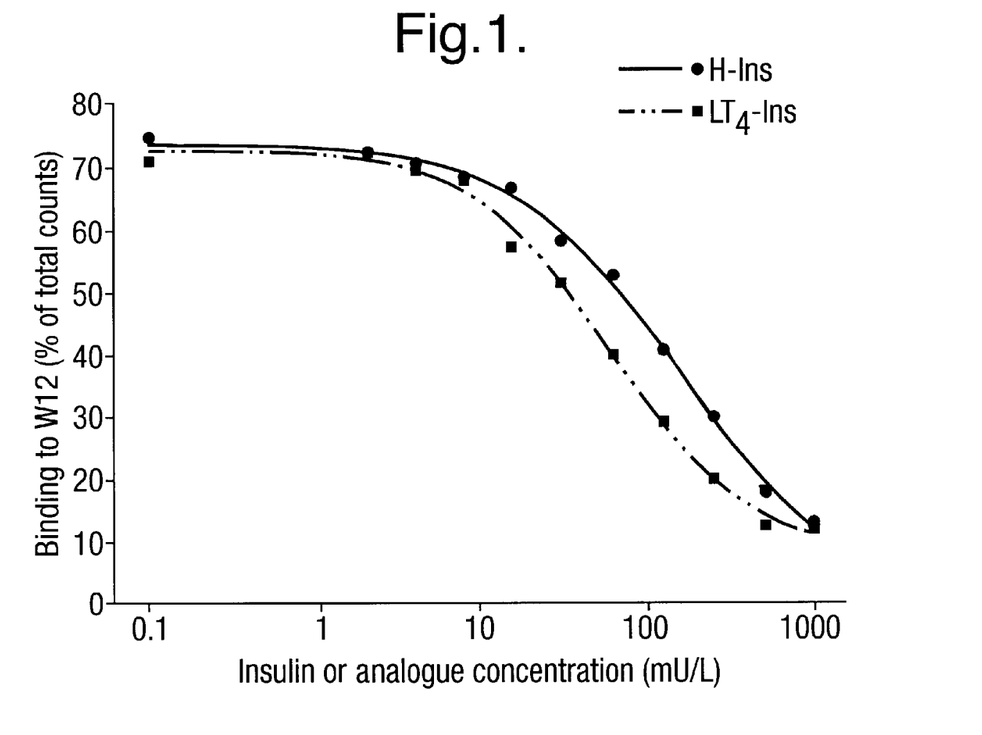

Double antibody RIA was used to quantify the immunoreactive insulin (IRI) in the FPLC fractions. The validity of using RIA to quantify the novel analogues, whose antibody binding behaviour was unknown, was confirmed by assaying standard solutions of H-Ins, and $LT_4$-Ins and FIG. 1 shows the inhibition of [$^{125}$I] insulin binding to the primary antibody W12 by H-Ins and the analogue. Their ED50s were 1065 pM (H-Ins), and 417.3 pM ($LT_4$-Ins). The standard curve for $LT_4$-Ins, was shifted to the left of the H-Ins curve, which could signify a lower binding to W12.

3.4.2 Fast Protein Liquid Chromatography (FPLC)

FPLC was used to study the binding of the insulin and the analogue to the THBPs (normal human serum, HSA 5% w/v, TBG 0.238 μM). IRI content in each fraction was assayed by RIA.

a) Non-Specific Binding of THBPs

Non-specific binding of the THBPs to the antibodies in RIA was measured by eluting the THBPs alone, and the fractions were assayed for IRI. They all showed negligible amounts of IRI.

b) Elution Profiles

Figure 2A:
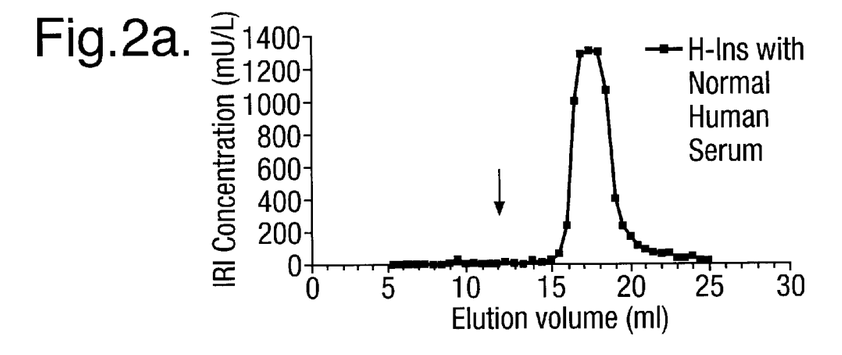
Figure 2B:
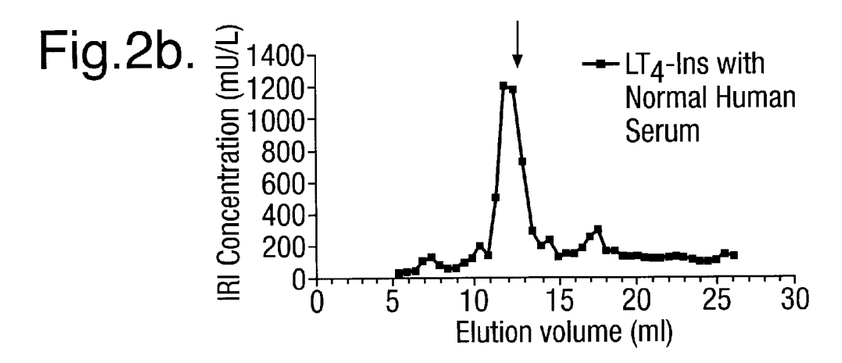
Figure 3A:
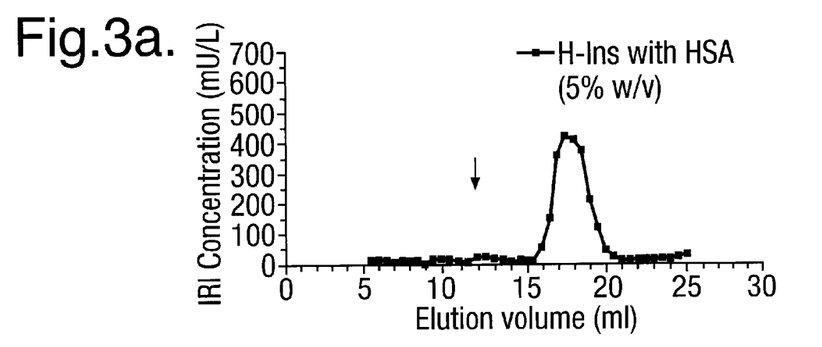
Figure 3B:
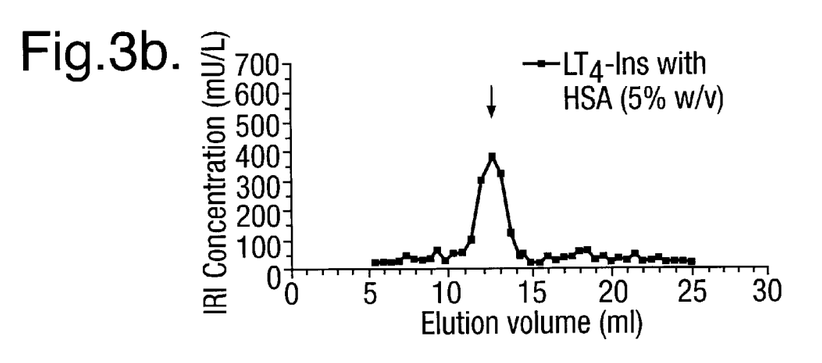
Figure 4A:
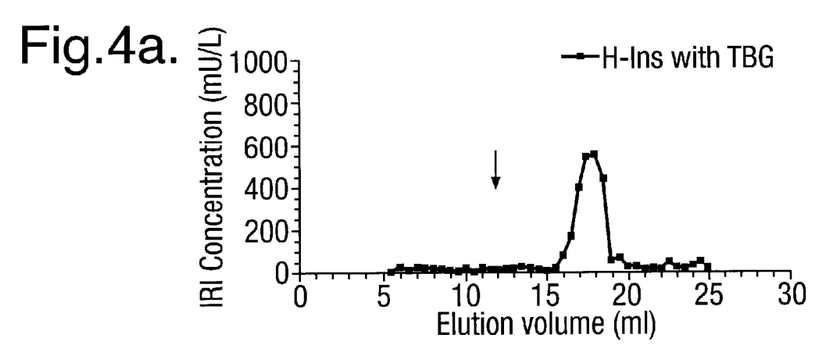
Figure 4B:
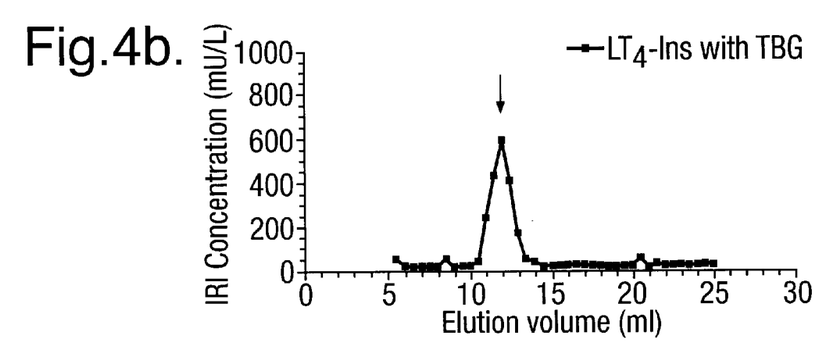

FIGS. 2a and b show the elution profiles of H-Ins, and LT$_4$-Ins, respectively after overnight incubation with the normal human serum. FIGS. 3a and b show the elution profiles of H-Ins and LT$_4$-Ins, respectively, after overnight incubation with 5% human serum albumin (HSA). FIGS. 4a and b show the elution profiles of H-Ins and LT$_4$-Ins, respectively, after overnight incubation with 0.238 μM TBG. The calculated % bound and % free values are included in Table 3. Appearances of the THBPs, as detected by UV absorbance on the original chromatogram (which was not sensitive enough to detect the analogues) are also indicated as arrows on the elution profiles. The shadowed box represents the bound fractions; the clear box represents free fractions.

H-Ins

The calculated % bound for H-Ins to each THBP was significantly lower than the % bound of the LT$_4$-Ins analogues to the same THBPs (p<0.05). Nevertheless, the % of bound H-Ins was not completely negligible. Background binding of 9.02% to HSA and 9.85% to TBG was observed (FIGS. 5A, 7A).

LT$_4$-Ins

The thyroxyl-linked analogue showed substantial binding (>60%) to the THBPs (Table 3), significantly higher than for unconjugated.

3.4.3 Equilibrium Binding Assays

Figure 5:
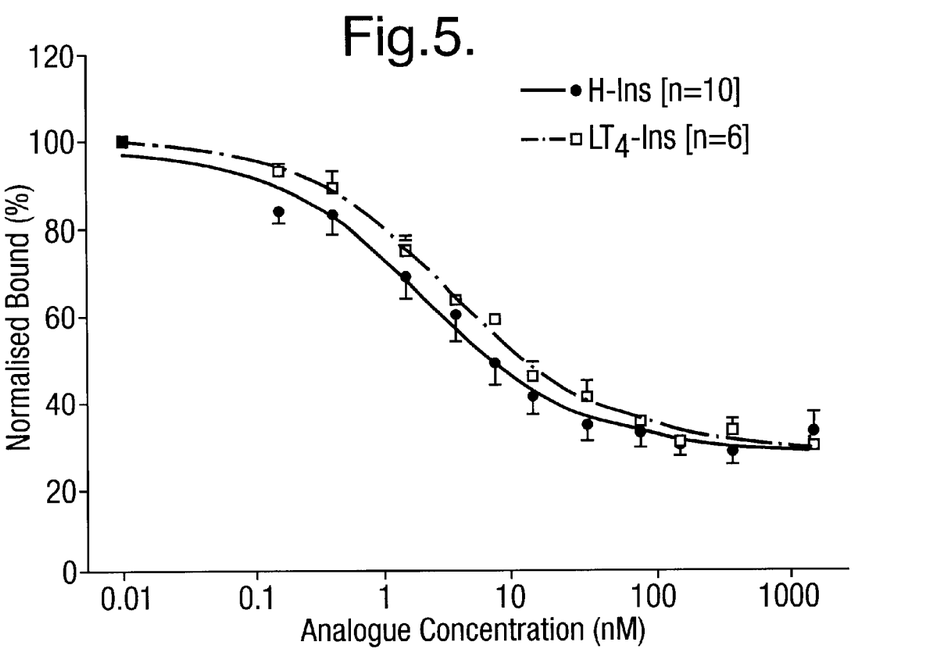

Equilibrium binding assays to insulin receptors on LPM were performed for H-Ins and LT$_4$-Ins. The binding curve of LT$_4$-Ins, is shifted to the right of the H-Ins curve (FIG. 5) and its ED50 (12.46±0.86) is significantly higher than H-Ins' (8.49±0.69) (p<0.05). This may be due to the T4 moieties shielding the insulin receptor from the insulin moiety.

The RPE of the analogue relative to H-Ins is 63.5% (40.5–96.7%).

TABLE 3

Binding of Analogues to THBPs in FPLC

| Analogue and THBP | Mean % Bound (fractions 5.5–15 ml) n = 3 | Mean % Free (fractions 15.5–25 ml) | Significant difference* |
|---|---|---|---|
| H-Ins | | | |
| 1. Normal human serum | 1.61 ± 0.47 | 98.39 | all others |
| 2. HSA (5% w/v) | 9.02 ± 3.12 | 90.98 | all others |
| 3. TBG | 9.85 ± 2.14 | 90.15 | all others |
| LT4-Ins | | | |
| 4. Normal human serum | 63.22 ± 0.12 | 36.78 | all others |
| 5. HSA (5% w/v) | 72.37 ± 2.31 | 27.63 | 2,11 |
| 6. TBG | 73.67 ± 3.41 | 26.33 | 3,9 |

% bound calculated as (total IRI in fractions 5.5–15 ml)/(total IRI in fractions 5.5–25 ml)
% free calculated as (total IRI in fractions 15.5–25 ml)/(total IRI in fractions 5.5–25 ml)
*Significantly different from other Ins with the same THBP (p < 0.05)
THBP = Thyroid hormone binding protein (normal human serum, HSA, TBG)
FPLC = Fast protein liquid chromatography
HSA = Human serum albumin
TBG = Thyroxine binding globulin
IRI = Immunoreactive insulin THBP=Thyroid hormone binding protein (normal human serum, HSA, TBG)
FPLC=Fast protein liquid chromatography
HSA=Human serum albumin
TBG=Thyroxine binding globulin
IRI=Immunoreactive insulin Example 4

4.1 In vivo Administration of LT$_4$-Ins in Human Subjects

Five normal human subjects received a subcutaneous bolus injection of either N$^{\alpha B1}$ L-thyroxyl-insulin (B1-LT4-Ins/B1-T4-Ins synthesised as in Example 1) or NPH insulin in random order. Insulin kinetics, relative effects on hepatic glucose production and peripheral glucose uptake were studied using euglycaemic clamp and stable isotope (D-6, 6-$^2$H$_2$ glucose) dilution techniques (Finegood, DT, et al, Diabetes 36, 914–927, 1987).

4.2 Method 4.2.1

The subjects were admitted to the metabolic ward at 07:00 h after an overnight fast. They were studied in a supine position and allowed water only to drink for the duration of the study. After a baseline blood sample for glucose isotope ratio measurement, a primed (170 mg) constant infusion (1.7 mg/min) of D-6,6-$^2$H$_2$ glucose (Mass Trace, Mass., USA) was administered for 17.5 h or less if the exogenous glucose requirements had returned to zero. The subjects were studied twice receiving either NPH insulin or B1-T4-Ins in randomised order with an interval of two weeks washout period between each treatment. The D-6,6-$^2$H$_2$ glucose infusion was allowed to equilibrate over 2 h followed by steady state baseline blood sampling every 10 minutes for a further 30 minutes. Subjects were then given a subcutaneous bolus injection of either NPH insulin (2.06 nmol/kg) or B1-T4-Ins (3.44 nmol/kg) at time 0 h (2.5 h into D-[6,6 $^2$H$_2$]glucose infusion) to the anterior abdominal wall.

4.2.2

After the bolus injection of the insulin or analogue blood samples were drawn at 15 min intervals for glucose determination and a variable infusion of dextrose (20%) was administered in order to maintain blood glucose at the basal concentration of each subject. The protocol was limited to a maximum of 15 h. Dextrose (20%) was premixed with D-[6,6 $^2$H$_2$]glucose (4 mg D-6,6-$^2$H$_2$ glucose/g of dextrose) in order to prevent the fall in tracer enrichment and consequent errors in glucose turnover calculations which otherwise occurs. The study was terminated at the time that the exogenous glucose requirements returned to zero or at 15 h after the insulin administration whichever was shorter.

4.2.3

Four Samples were collected for basal measurements of insulin, c-peptide and glucose concentrations and glucose enrichment. A sample was also taken for basal measurements of IGF-I, glucagon, thyroid hormones, thyroid hormone stimulating hormone (TSH) and non-esterified free fatty acid (NEFA). After administration of NPH insulin or B1-T4-Ins samples were taken every 30 min for the determination of insulin or analogue, c-peptide and glucose concentrations and for glucose enrichment. Samples were taken every 3 h for the measurement of NEFA and glucagon and every 5 h for measurement of IGF-I, free T4, free T3 and TSH concentrations. A sample was also taken after 24 h (after breakfast) for the determination of insulin or analogue and thyroid hormones concentrations. Serum samples also were taken at 0, 3, 8, 24 h for fast protein liquid chromatography (FPLC) analysis. Serum and plasma samples were separated immediately and stored at −20° C. until assayed.

4.2.4

Immunoreactive insulin (IRI) and IGF-I concentrations in serum samples and C-peptide in plasma were determined by double antibody radioimmunoassay (RIA) as previously described in example 3. The within assay coefficients of variation (CV) were 7%, 7% and 6% respectively. Thyroxyl-insulin analogue concentration (IRI) in serum samples and in the FPLC fractions were determined by a double antibody RIA (CV 8%). Glucagon concentration in plasma samples was measured by RIA using a commercially available kit from Linco Research Inc. (St. Louis, Mo., USA).

Glucose concentration in the plasma samples was determined by a glucose oxidase method using a Clandon Scientific Glucose Analyser, (Yellow Springs Instruments, Yellow Spring, Ohio, USA).

NEFA concentration in serum samples was determined using a commercially available kit from Wako Chemicals GmbH (Neuss, Germany).

Glucose isotopic enrichment was determined by gas chromatography mass spectrometry (GCMS) on a VG Trio-2 5890 (VG Micromas, Manchester, UK.) using selected ion monitoring of a glucose penta-acetate derivative. The ions monitored were of molecular mass 242 and 244 representing $[M—C_5O_5H_8]^+$ and the corresponding fragment enriched with two deuterium atoms, respectively. The within assay C.V. was <2%.

4.2.5

To determine the status of the thyroxyl-insulin analogues (bound or free) in the serum samples from infusion studies, samples were subjected to FPLC separation.

4.3 Results 4.3.1 Tolerability

B1-T4-Ins was extremely well tolerated. None of the subjects suffered any significant side effect.

4.3.2 Serum Insulin and Analogue Concentrations

Figure 6:
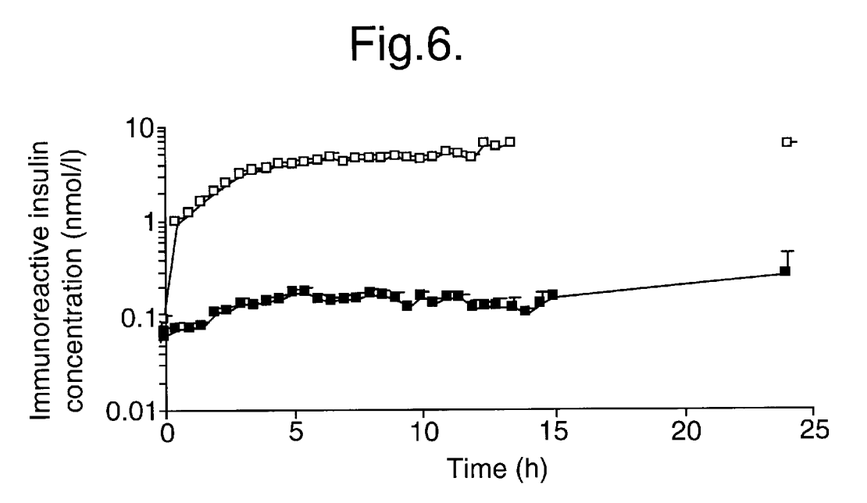

FIG. 6 shows the immunoreactive serum insulin or total analogue concentrations after a suncutaneous injection of NPH insulin (closed symbols) and B1-T4-Ins (open symbols) during clamp studies, n=5. Values are mean±SEM.

Following bolus injection of B1-T4-Ins total immunoreactive insulin/analogue (IRI) concentration in serum increased from basal value of 0.08 (95% confidence intervals 0.06 and 1.01) nmol/l to 0.97 (0.61 and 1.33) nmol/l and 4.02 (2.84 and 5.20) nmol/l at 30 min and 6 h respectively (p<0.01). These elevated IRI concentrations persisted throughout the study (FIG. 6).

Following bolus injection of NPH insulin, serum IRI concentration increased from a basal value of 0.06 (0.03 and 0.09) nmol/l to 0.07 (0.02 and 0.09) nmol/l and 0.15 (0.1 and 0.2) nmol/l at 30 min and 6 h respectively (p<0.01).

The increase in immunoreactive insulin/analogue concentration from basal level with B1-T4-Ins (0.89 (1.22 and 0.76) nmol/l was significantly different from that of NPH insulin (0.014 (0.01 and 0.03) nmol/l.

IRI concentration post-breakfast at 24 h after B1-T4-Ins was 4.18 (3.31 and 5.05) nmol/l, significantly higher than that after NPH insulin 0.24 (0.02–0.48) nmol/l, (p<0.05).

4.3.3 C-peptide Concentrations

C-peptide concentration did not change from the basal level 0.41 (0.28 and 0.54) nmol/l during the study with B1-T4-Ins but fell significantly from its basal level 0.41 (0.38 and 0.50) nmol/l to 0.30 (−0.47 and1.77) nmol/l towards the end of the study with NPH insulin (11–15 h), p<0.05.

4.3.4 FPLC Fractionation of Serum Samples

Immunoreactive insulin after injection of NPH insulin eluted at 15–20 ml, corresponding to the native H-Ins peak (i.e. <12000 Da).

Immunoreactive analogue after injection of T4-Ins (at times 3, 8, 24 h) eluted mostly (86%, 86%, 86%,) between 5–15 ml, corresponding to high molecular weight IRI (i.e.: bound form ≈60000 Da). The remaining IRI in the sample eluted between 15–20 ml (i.e. free form <12000 Da).

4.3.5 Euglycaemic Clamp

Fasting plasma glucose concentration was 5.3 (5.0 and 5.6) mmol/l and euglycaemia was maintained during the clamp (glucose concentration of 5.2 (4.5 and 5.9) mmol/l).

4.3.6 Exogenous Glucose Infusion Rates (GIR)

Figure 7:
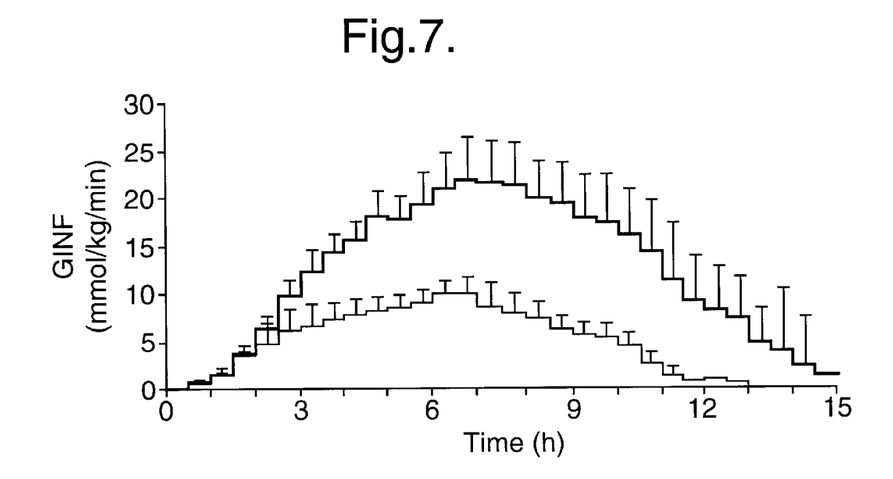

FIG. 7 shows the exogenous glucose infusion rates achieved during euglycaemic clamp studies after a subcutaneous injection of NPH insulin (thick line) and B1-T4-Ins (thin line), n=5. Values are mean±SEM.

The mass of glucose required to maintain euglycaemia throughout each experiment was calculated from the record of the glucose infusion rates (AUC GIR). AUC GIR to maintain euglycaemia following injection of NPH insulin (10.73 (5.77 and 15.69) mmol/kg) was significantly greater than the AUC calculated following injection of B1-T4-Ins (4.04 (1.73 and 6.35) mmol/kg) (p=0.027) (Table 4 and FIG. 7). The duration of action for B1-T4-Ins 672 (579 and 765) min was not different from that of NPH insulin 765 (631 and 899) min. Starting times for exogenous glucose infusion for B1-T4-Ins and NPH insulin was also similar (45 (28 and 62) min compared to 67 (19 and 115) min, respectively).

4.3.7 Glucose Appearance Rate: Endogenous Glucose (Ra)

Figure 8:
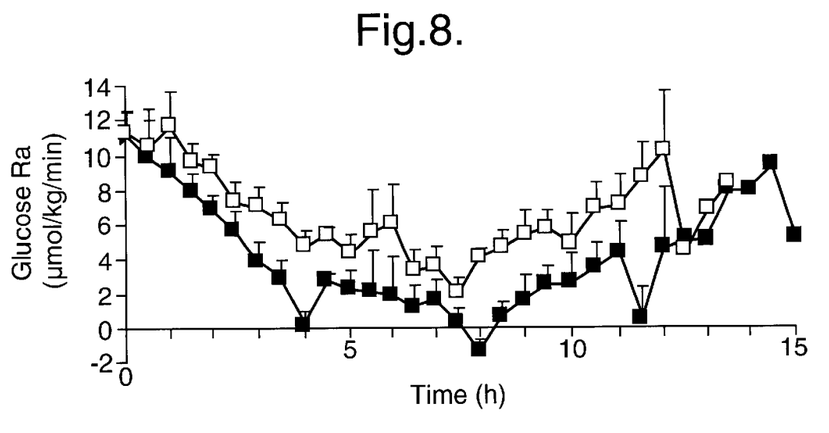

FIG. 8 shows glucose appearance rate (Ra) achieved during euglycaemic clamp studies after a subcutaneous injection of NPH insulin (closed symbols) and B1-T4-Ins (open symbols), n+5. Values are mean±SEM.

The AUCRa values following injection of either NPH insulin or B1-T4-Ins were not different, (Table 4 and FIG. 8), suggesting similarity of action on the liver at the dose used.

4.3.8 Glucose Disposal Rates

Figure 9A:
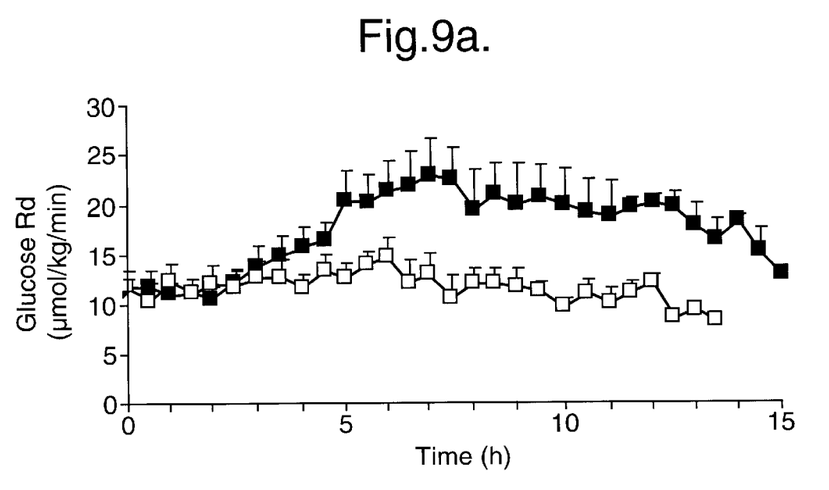
Figure 9B:
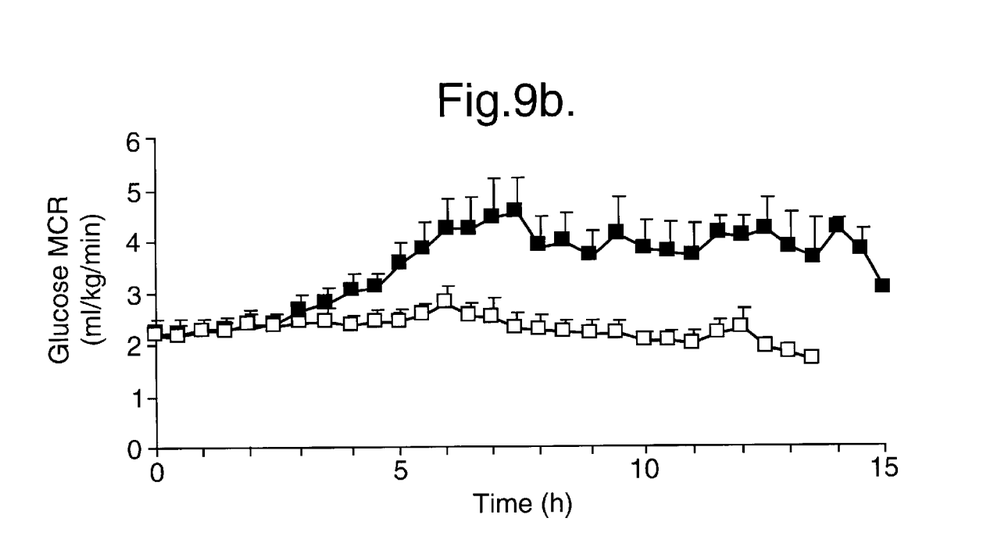

FIG. 9 shows glucose disposal (Rd; FIG. 9a) and metabolic clearance rate of glucose (MCR; FIG. 9b) achieved during euglycaemic clamp studies after a subcutaneous injection of NPH insulin (closed symbols) and B1-T4-Ins (open symbols), n-5. Values are mean±SEM.

Glucose disposal rates (Rd) significantly increased from basal levels 11.07 (8.64 and 13.50) μmol/kg/min after NPH insulin injection (p=0.01) but not after B1-T4-Ins. AUCRd following injection of NPH insulin was greater than that of AUCRd following B1-T4-Ins injection (p=0.025), Table 4 and FIG. 9.

4.3.9 Metabolic Clearance Rate of Glucose (MCR)

Glucose MCR significantly increased from basal levels after NPH insulin injection (p=0.01) but not after B1-T4-Ins. The AUC for glucose MCR following injection of NPH insulin was significantly different from the AUC for glucose MCR following B1-T4-Ins injection (p=0.002) (Table 4, FIG. 9).

4.3.10 Non-esterified Fatty Acid Concentrations

Figure 10:
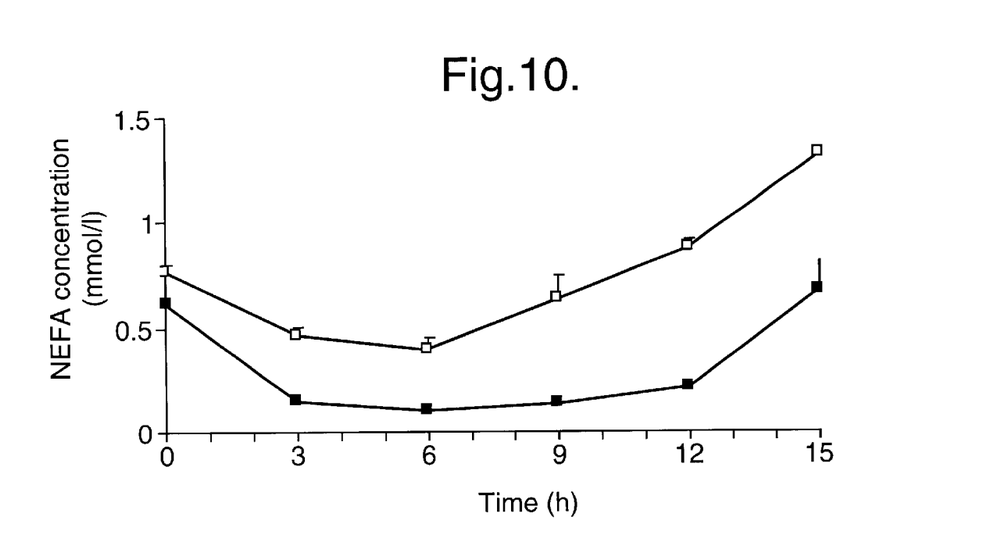

FIG. 10 shows non-esterified fatty acid concentration (mmol/l) during euglycaemic clamp studies after a subcutaneous injection of NPH insulin (closed symbols) and B1-T4-Ins (open symbols), n=5. Values are mean±SEM.

NEFA concentration was suppressed significantly from basal levels (0.69 (0.56 and 0.82) μmol/l) with both B1-T4-Ins and NPH insulin at 3 hrs to 0.46 (0.36 and 0.56) μmol/l and 0.15 (0.07 and 0.22) μmol/l, respectively. The reduction of NEFA concentration after administration of NPH insulin was greater at every time-point than after B1-T4-Ins administration (p<0.05) (FIG. 10).

4.3.11 Effect on Other Hormones

Concentrations of IGF-I, glucagon, thyroid stimulating hormone (TSH), fT3 and fT4 did not change during either of the protocols.

TABLE 4

|  | Glucose infusion rate AUC (mmol × kg$^{-1}$) | Glucose Rd AUC (mmol × kg$^{-1}$) | Glucose MCR AUR (mmol × kg$^{-1}$) | Glucose Ra AUC (mmol × kg$^{-1}$) |
|---|---|---|---|---|
| Insulin | 10.73 (5.77 and 15.69) | 4.95 (1.17 and 8.73) | 1.03 (0.41 and 1.65) | −5.63 (−7.3 and −3.96) |
| B1-LT4-Ins | 4.04* (1.73 and 6.35) | 0.49† (−0.97 and 1.95) | 0.15‡ (0 and 0.3) | −3.32 ± 2.57 (−5.89 and −.75) |

*p = 0.027,
†p = 0.025,
‡p = 0.002

4.4 Conclusions

This study reports the first administration of a covalently linked thyroxyl insulin analogue to human subjects. We have shown that $N^{\alpha B1}$L-thyroxyl-insulin is well tolerated, well absorbed following subcutaneous administration, has a long duration of action and appears to confer hepatoselectivity when compared to NPH insulin.

Although in these experiments no change in TSH was observed, in studies using rats rendered hypothyroid by treatment with polythiouracil for one week B1-T4-Ins administration by intra-peritoneal injection was associated with a dose dependent suppression of TSH concentration (F. Shojaee-Moradie, unpublished data).

Example 5
Insulin Receptor Binding Studies with IM-9 Lymphocytes

Receptor binding was determined in competition assays with [Tyr-($^{125}$I)$^{A14}$]-Insulin in cultured IM-9 Lymphocytes. Because of the designed affinity of the fatty acid substituted insulin B1-T1LT4-Ins towards serum albumin the standard 1% solution of BSA was replaced by 1% γ-globulin (suppression of non-specific binding).

Relative binding was calculated using the program Prism via non-linear curve-fitting.

The binding of $LT_4$-Insulin (synthesised according to Example 1) determined by this technique is reduced to 49.8% of that of insulin.

Example 6
Binding Studies of TBG—Optical Biosensor Studies

An optical biosensor IASys is used to record binding of LT4-Ins to TBG.

The optical bio-sensor IAsys makes it possible to record biomolecular interactions in real time and thus kinetical studies. We studied the binding of the Thyroid-Insulin-conjugate B1-LT4-Insulin synthesis as in Example 1 to the plasma protein thyroxine binding globulin(TBG).

The surface of the cuvette is covered with a carboxymethylated dextran matrix (CMD), to which the plasma protein TBG is immobilized.

Immobilization of TBG to the carboxymethylated matrix is detected via the change of the resonance angle.

For the kinetical studies the Thyroid-Insulin conjugate was injected into the microcuvette in dilution series of 200, 300, 400 and 500 μg/ml in HBS/Tween-buffer at 25° C. To test for reproducibility, all measurements were repeated 3 times.

As a control, native insulin was injected at high concentration (500 μg/ml). While injection leads to a buffer-jump, association cannot be observed. Removal of the insulin solution and injection of blank buffer caused another buffer-jump, but there was no sign of dissociation. Thus, non-specific binding of insulin to the immobilized plasma protein can be excluded. For further measurements the surface of the microcuvette was rinsed several times with buffer.

Determination of "on-rate" constants $k_{on}$ at various ligand concentrations $C_L$ allow $k_{on}$ to be plotted against $C_L$ according to equation (4). This gives the association rate constant $k_A$ from the slope and the dissociation rate constant $k_D$ at $C_2=O$. It has, however, to be taken into account that the error of $k_D$ becomes too large when $k_D<0,01$ s$^{-1}$ (IAsys, METHODS GUIDE).

$$k_{on}=k_D+k_A \cdot c_L \qquad (4)$$

In the binding studies with Thyroid Insulin conjugates to immobilized TBG the good reproducibility of the individual determinations has to be noted.

The association and dissociation curves of the Thyroid Insulin conjugate indicated in Table 3 were analyzed with the program Fast-fit. For quantification of association single-phasic curve-fitting was chosen, since the values for two-phase fitting showed larger fluctuations.

The association rate constant of LT4-ins is (3.23±D.89) $10^5$ M$^{-1}$ S$^{-1}$.

Evaluation of dissociation was also via single phase curve-fitting, for the same reasons as above. The dissociation constants $k_D$ of LT4-Ins is (5.56±2.39) $10^{-2}$ M$^{-1}$ S$^{-1}$.

What is claimed is:

1. A conjugate compound derived from a pharmaceutical active whose molecular weight is less than 25,000 Daltons comprising: a pharmaceutical active whose molecular weight is less than 25,000 Daltons covalently linked to a pendant molecular moiety, said pendant molecular moiety having an affinity for one or more binding proteins present in the human or animal circulatory system.

2. A conjugate compound according to claim 1, which is an insulin analogue and which comprises an insulin or functional equivalent thereof covalently linked to the pendant molecular moiety.

3. A conjugate compound according to claim 1, wherein the pendant molecular moiety is a naturally occurring hormone or an analogue of a naturally occurring hormone.

4. A conjugate compound according to claim 3, wherein the pendant molecular moiety is a thyroid hormone.

5. A conjugate compound according to claim 4 wherein the thyroid hormone is thyroxine.

6. A conjugate compound according to claim 2, wherein the pendant molecular moiety is a naturally occurring hormone or an analogue of a naturally occurring hormone.

7. A conjugate compound according to claim 6, wherein the pendant molecular moiety is a thyroid hormone.

8. A conjugate compound according to claim 7, wherein the thyroid hormone is thyroxine.

9. A conjugate compound according to claim 8 in which the thyroxine is 3, 5, 3', 5'-tetraiodo-l-thyronine.

10. A conjugate compound according to claim 2, in which the insulin or functional equivalent thereof is covalently linked to the said pendant molecular moiety through its B1 terminal amino group.

11. A conjugate compound according to claim 1 in which the said binding protein is thryoxine binding globulin.

12. A conjugate compound derived from a pharmaceutical active whose molecular weight is less than 25,000 Daltons, comprising a pharmaceutical active covalently bound to a pendant molecular moiety which is a thyroid hormone or derivative analogue thereof.

13. A conjugate compound according to claim 12, wherein the thyroid hormone is thyroxine.

14. A conjugate compound according to claim 13, in which the thyroxine is 3, 5, 3', 5'-tetraiodo-L-thyronine.

15. A conjugate compound according to claim 11, in which the pharmaceutical active is insulin or a functional equivalent thereof.

16. A conjugate compound according to claim 15, in which the said thyroid hormone is covalently bound to the B1 amine group of insulin or functional equivalent.

17. A pharmaceutical composition comprising a conjugate compound derived from a pharmaceutical active whose molecular weight is less than 25,000 Daltons comprising: a pharmaceutical active whose molecular weight is less than 25,000 Daltons covalently linked to a pendant molecular moiety, said pendant molecular moiety having an affinity for one or more binding proteins present in the human or animal circulatory system.

18. A pharmaceutical composition comprising a conjugate compound derived from a pharmaceutical active whose molecular weight is less than 25,000 Daltons, comprising a pharmaceutical active covalently bound to a pendant molecular moiety which is a thyroid hormone or derivative or analogue thereof.

* * * * *